United States Patent
Laufer et al.

(10) Patent No.: US 6,432,988 B1
(45) Date of Patent: Aug. 13, 2002

(54) 2-ARYLALKYLTHIO -IMIDAZOLES, 2-ARYLALKENYL -THIO -IMIDAZOLES AND 2-ARYLALKINYL -THIO -IMIDAZOLES AS ANTI -INFLAMMATORY SUBSTANCES AND SUBSTANCES INHIBITING THE RELEASE OF CYTOKINE

(75) Inventors: Stefan Laufer, Blaubeuren; Hans-Günter Striegel, Blaustein; Karola Neher, Blaubeuren, all of (DE)

(73) Assignee: Merckle GmbH, Blaubeuren (DE)

( * ) Notice: Subject to any disclaimer, the term of this patent is extended or adjusted under 35 U.S.C. 154(b) by 0 days.

(21) Appl. No.: 09/787,390

(22) PCT Filed: Sep. 20, 1999

(86) PCT No.: PCT/EP99/06945

§ 371 (c)(1),
(2), (4) Date: May 11, 2001

(87) PCT Pub. No.: WO00/17192

PCT Pub. Date: Mar. 30, 2000

(30) Foreign Application Priority Data

Sep. 18, 1998 (DE) .......................... 198 42 833

(51) Int. Cl.$^7$ ...................... A61K 31/44; C07D 401/14
(52) U.S. Cl. .................................. 514/341; 546/274.1
(58) Field of Search ......................... 546/274.1; 514/341

(56) References Cited

U.S. PATENT DOCUMENTS

| 3,940,486 A | 2/1976 | Fitzi ........................... 424/263 |
| 4,402,960 A | 9/1983 | Niedballa et al. ........... 424/251 |
| 4,461,770 A | 7/1984 | Ferrini et al. ................ 424/263 |
| 4,528,298 A | 7/1985 | Niedballa et al. ........... 514/398 |
| 4,584,310 A | 4/1986 | Ferrini et al. ................ 514/397 |
| 4,585,771 A | 4/1986 | Klose et al. ................. 514/220 |
| 5,656,644 A | 8/1997 | Adams et al. ............... 514/341 |

FOREIGN PATENT DOCUMENTS

| WO | WO 93/14081 A1 | 7/1993 |
| WO | WO 95/00501 A2 | 1/1995 |
| WO | WO 96/03387 A1 | 2/1996 |
| WO | WO 99/03837 A1 | 1/1999 |

OTHER PUBLICATIONS

CA Reference 129:67734t "Synthesis and antimicrobial evaluation of some new imidazole 2–sulfones.", vol. 129, No. 6, 1998, p. 664.*

Boehm, J. et al; "1–Substituted 4–Aryl–5–pyridinylimidazoles: A New Class of Cytokine Suppressive Drugs with Low 5–Lipoxygenase and Cyclooxygenase Inhibitory Potency"; J. Med. Chem.; 1996; pp 3929–3937; vol. 39; American Chemical Society.

Gallagher, T. et al; "2,4,5–Triarylimidazole Inhibitors of IL–1 Biosynthesis"; Bioorganic & Medical Cemistry Letters; 1995; pp 1171–1175; vol. 5; Elesevier; 1995; Great Britain.

Wilson, K. et al; "The Structural Basis for the Specificity of Pyridinylimidazole Inhibitors of p38 MAP Kinase"; Chemistry & Biology; Jun. 1997; pp 423–431; vol. 4; Current Biology Ltd.

Lantos, I. et al; "Antiinflammatory Activity of 5,6–Diaryl–2, 3–dihydroimidazo [2,1–b]thiazoles. Isomeric4–Pyridyl and 4–Substituted Phenyl Derivatives"; J. Med. Chem.; 1984; pp 72–75; vol. 27; The American Chemical Society, 1983.

\* cited by examiner

*Primary Examiner*—Alan L. Rotman
*Assistant Examiner*—Binta Robinson
(74) *Attorney, Agent, or Firm*—Heller Ehrman White and McAuliffe

(57) ABSTRACT

The invention relates to 4-heteroaryl-5-phenylimidazole derivatives having 2-arylalkylthio, 2-arylalkenylthio and 2-arylalkynylthio substitution, of the general formula I:

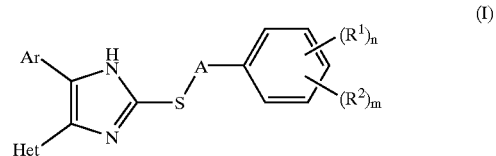

in which Ar is a phenyl radical, Het is a hetero aromatic radical, A is an alkylene chain, $R^1$ is an alkylthio, alkylsulfinyl, alkylsulfonyl, sulfonamido or alkylcarbonyl group and $R^2$ is an alkyl, hydroxyl, alkoxy, alkoxycarbonyl, sulfonamido, carboxyl, nitro or aminocarbonyl group or a halogen atom. n can be 1 or 2 and m is 0 to 2. The compounds according to the invention show antiinflammatory activity.

14 Claims, No Drawings

2-ARYLALKYLTHIO-IMIDAZOLES, 2-ARYLALKENYL-THIO-IMIDAZOLES AND 2-ARYLALKINYL-THIO-IMIDAZOLES AS ANTI-INFLAMMATORY SUBSTANCES AND SUBSTANCES INHIBITING THE RELEASE OF CYTOKINE

The present invention relates to 2-arylaklylthioimidazole, 2-arylalkenylthioimidazole and 2-arylalkynylthioimidazole derivatives, a process for their preparation and medicaments which contain these imidazole derivatives.

It is known that various imidazole derivatives have an antiinflammatory activity. Inter alia, compounds having 4,5-di(hetero)arylimidazole structural elements have been investigated in detail.

Thus U.S. Pat. No. 5,656,644 and WO 93/14081 disclose 4-aryl-5-heteroarylimidazole derivatives which are substituted in the 2-position by an optionally substituted aryl or heteroaryl group and which have an inhibitory activity on the release of cytokines such as IL-1, IL-6, IL-8 and TNF.

U.S. Pat. No. 3,940,486 discloses 4(5)-phenyl-5(4)-heteroarylimidazole derivatives which are substituted in the 2-position by an alkyl, cycloalkyl or phenyl radical. Various pharmaceutical actions of these compounds, such as an antiinflammatory activity, are mentioned.

U.S. Pat. No. 4,585,771 discloses 4,5-diphenylimidazole derivatives which are substituted in the 2-position by a pyrrolyl, indolyl, imidazolyl or thiazolyl radical.

These compounds have an antiinflammatory and antiallergic activity.

U.S. Pat. Nos. 4,528,298 and 4,402,960 disclose 4,5-di(hetero)arylimidazole derivatives which are substituted in the 2-position by a thio, sulfinyl or sulfonyl group having a phenyl, pyridyl, N-oxypyridyl, pyrimidinyl, thiazolyl or thienyl radical. These compounds have an antiinflammatory and antiallergic activity.

U.S. Pat. Nos. 4,461,770 and 4,584,310 disclose 4(5)-aryl-5(4)-heteroarylimidazole derivatives which are substituted in the 2-position by a thio, sulfinyl or sulfonyl group having a substituted or unsubstituted aliphatic hydrocarbon radical. The substituted or unsubstituted aliphatic hydrocarbon radical is, for example, a phenyl-$C_{1-4}$-alkyl group in which the phenyl radical can be substituted by $C_{1-4}$-alkyl, $C_{1-4}$-alkoxy, halogen having an atomic weight of not more than 35, nitro, amino or N,N-di-$C_{1-4}$-alkylamino. These compounds have, inter alia, an antiinflammatory activity. 4,5-Diaryl-substituted imidazoles as cyclooxygenase-2-inhibitors are disclosed in WO 95/00501.

The molecular target of the 4-(4-fluorophenyl)-5-(4-pyridyl)imidazole derivatives is described by Wilson K. P. et al. (Chemistry & Biology (1997), 4, 423–431) and Young P. R. et al. (J. Biol. Chem. (1997), 272, 12116–12121) as the p38 MAP kinase (mitogen-activatable kinase) activated in the signal transduction of inflammatory stimuli in a phosphorylation cascade, and a serine threonine kinase (Cobb, M. H., Goldsmith, E. J., J. Biol. Chem. (1995), 270, 14843–14846). According to Wilson K. P. et al. and Young P. R. et al., the structural element competes with ATP for binding to the ATP binding site of the kinase center (for this cf. Tong et al. & Pargellis, C. A. Nat.Struct. Biol. 4, (1997) 311–316).

Other 1,2-diaryl-substituted heteroaromatic systems additionally show a high affinity for enzyme systems of the arachidonic acid cascade, whose metabolic products exert decisive influence on the inflammatory process. It is seen that with suitable choice of the substituents, of the aromatics flanking the heterocycle, a favorable combination effect takes place on targets such as 5-lipoxygenase, cyclooxygenase-1 and -2 and p38 MAP kinase (TNF-α, IL-1β release).

Despite numerous known compounds, a need furthermore exists for substances having antiinflammatory activity, which inhibit the release of various cytokines and serve as inhibitors of the mediators of the arachidonic acid cascade. In particular, a need exists for compounds which do not only act on the parameters which are decisive in the acute course of inflammatory diseases (mediators of inflammation), but which can also intervene in the immunological processes crucial to the chronic course (cytokine release, expression of cell-surface antigens).

One object of the present invention consists in making such compounds available.

It has now surprisingly been found that 4-heteroaryl-5-phenylimidazole derivatives which are substituted in the 2-position by a phenylalkylthio group whose phenyl radical is in turn substituted by an alkylthio, alkylsulfinyl, alkylsulfonyl, sulfonamido or aklycarbonyl group achieve this object.

The present invention thus relates to a compound of the general formula I:

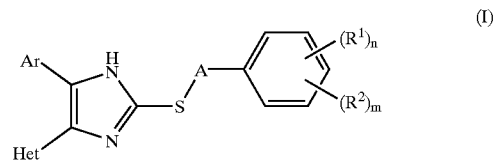

in which
Ar is a phenyl radical which can optionally be substituted by one or more substituents, selected from halogen, $C_{1-4}$-alkyl, $C_{1-4}$-alkoxy and $C_{1-4}$-alkylthio;
Het is a pyridyl, pyrimidinyl or pyrazinyl radical which can optionally be substituted by one or more substituents selected from halogen, amino, $C_{1-4}$-alkylamino, $C_{1-4}$-alkyl, hydroxyl, $C_{1-4}$-alkoxy or $C_{1-4}$-alkylthio;
A is a straight-chain or branched, saturated or unsaturated alkylene chain having up to 6 carbon atoms;
$R^1$ is $C_{1-4}$-alkylthio, $C_{1-4}$-alkylsulfinyl, $C_{1-4}$-alkylsulfonyl, sulfonamido or $C_{1-4}$-alkylcarbonyl;
$R^2$ is halogen, $C_{1-4}$-alkyl, hydroxyl, $C_{1-4}$-alkoxy, $C_{1-4}$-alkoxycarbonyl, sulfonamido, carboxyl, nitro or aminocarbonyl;
n is 1 or 2 and
m is 0 to 2
or a pharmaceutically tolerable salt thereof.

"Alkyl" is presently understood as meaning a lower alkyl group having up to 4 C atoms, which can be straight-chain or branched. This includes, for example, methyl, ethyl, propyl, isopropyl, butyl, isobutyl and tert-butyl.

"Alkoxy", "alkylthio", "alkylamino", "alkylsulfinyl", "alkylsulfonyl", "alkylcarbonyl" and "alkoxycarbonyl" are presently in each case understood as meaning a group which contains an alkyl group defined above.

"Halogen" is presently understood as meaning fluorine, chlorine, bromine and iodine, preferably fluorine, chlorine and bromine and in particular fluorine.

A "straight-chain or branched, saturated or unsaturated alkylene chain having up to 6 carbon atoms" is presently understood as meaning a $C_{1-6}$-alkylene chain, such as methylene, ethylene, 1,3-propylene, 1-methylethylene, 2-methylethylene, 1,4-butylene, 1-methyl-1,3-propylene, 2-methyl-1,3-propylene, 3-methyl-1,3-propylene, 1-ethylethylene, 2-ethylethylene, 2,3-dimethylethylene and 2,2-dimethyl-1,3-propylene, a $C_{3-6}$-alkenylene chain having one or more double bonds, such as propenylene and allenylene, and a $C_{3-6}$-alkynylene chain having one or more triple bonds, such as propynylene and butynylene. The straight-chain or branched, saturated or unsaturated alkylene chain A is preferably a straight-chain, saturated alkylene chain having 1 to 4 carbon atoms, preferably 1 or 2 carbon atoms, namely methylene or ethylene.

The heteroaromatic radical Het in the compound of the general formula I is pyridyl, pyrimidinyl or pyrazinyl, where these heteroaromatic radicals can optionally be substituted. The substituent is preferably a halogen, or an amino group. Particularly preferably, the heteroaromatic radical Het is 4-pyridyl, 3-aminopyridyl, 2,4-pyrimidinyl or 3-amino-2,4-pyrimidinyl.

The substituents by which the phenyl radical Ar in the compound of the general formula I can each be substituted are preferably fluorine, chlorine, bromine, $C_{1-4}$-alkyl, $C_{1-4}$-alkoxy or $C_{1-4}$-alkylthio. Particularly advantageously, the phenyl radical Ar is substituted in the para-position by fluorine, methoxy or methylthio.

The phenyl radical Ar is particularly preferably a 4-fluorophenyl group.

The phenyl group of the phenylalkylthio radical which substitutes the imidazole base unit in the compound of the general formula I in the 2-position, is substituted according to the invention by at least one group $R^1$, but at most by two groups $R^1$. The substituent $R^1$ is a $C_{1-4}$-alkylthio, $C_{1-4}$-alkylsulfinyl, $C_{1-4}$-alkylsulfonyl, sulfonamido or $C_{1-4}$-alkylcarbonyl group, where $R^1$ is advantageously a methylthio, methylsulfinyl, methylsulfonyl, sulfonamido or acetyl group.

The phenyl group of the phenylalkylthio radical which substitutes the imidazole base unit in the compound of the general formula I in the 2-position can include further substituents $R^2$. These substituents $R^2$ are $C_{1-4}$-alkyl, $C_{1-4}$-alkoxy, $C_{1-4}$-alkoxycarbonyl, sulfonamido, carboxyl, hydroxyl, nitro and aminocarbonyl, and also halogen, such as fluorine, chlorine, bromine and iodine. The phenyl radical in the phenylalkyl side chain of the compound of the general formula I can have from 0 to 2 substituents $R^2$, which can be identical or different. Compounds of the general formula I are preferred here in which n is 1 and m is 0–2.

Compounds of the general formula I have proven particularly advantageous in which the phenyl radical Ar is a 4-fluorophenyl group, the heteroaromatic radical Het is a 4-pyridyl, 3-aminopyridyl, 2,4-pyrimidinyl or 3-amino-2,4-pyrimidinyl group, A is methylene or ethylene, n is 1 and m is 0–2.

The following compounds of the general formula I may be mentioned by way of example:
5-(4-fluorophenyl)-2-[(4-methylthiophenyl)methylthio]-4-pyridylimidazole
5-(4-fluorophenyl)-2-[(4-methylsulfinylphenyl) methylthio]-4-pyridylimidazole;
5-(4-fluorophenyl)-2-[(4-methylsulfonylphenyl) methylthio]-4-pyridylimidazole;
2-[(4-aminosulfonylphenyl)methylthio]-5-(4-fluorophenyl)-4-pyridylimidazole;
2-[2-(4-aminosulfonylphenyl)ethylthio]-5-(4-fluorophenyl)-4-pyridylimidazole;
5-(4-fluorophenyl)-2-[2-(4-methylthiophenyl)ethylthio]-4-pyridylimidazole;
5-(4-fluorophenyl)-2-[2-(4-methylsulfonylphenyl) ethylthio]-4-pyridylimidazole;
5-(4-fluorophenyl)-2-[(3-methylthiophenyl)methylthio]-4-pyridylimidazole;
5-(4-fluorophenyl)-2-[(2-methylthiophenyl)methylthio]-4-pyridylimidazole;
5-(4-fluorophenyl)-2-[(3-methylsulfinylphenyl) methylthio]-4-pyridylimidazole;
5-(4-fluorophenyl)-2-[(2-methylsulfinylphenyl) methylthio]-4-pyridylimidazole;
5-(4-fluorophenyl)-2-[(4-hydroxy-3-methylthiophenyl) methylthio]-4-pyridylimidazole;
5-(4-fluorophenyl)-2-[(4-hydroxy-3-methylthiophenyl) methylthio]-4-pyridylimidazole;
2-[(5-chloro-2-hydroxy-3-methylthiophenyl)methylthio]-5-(4fluorophenyl)-4-pyridylimidazole; and
2-[(5-chloro-2-hydroxy-3-methylsulfinylphenyl) methylthio]-5-(4-fluorophenyl)-4-pyridylimidazole.

It should be taken into account that in the case of the compounds according to the invention the following structural equilibrium exists:

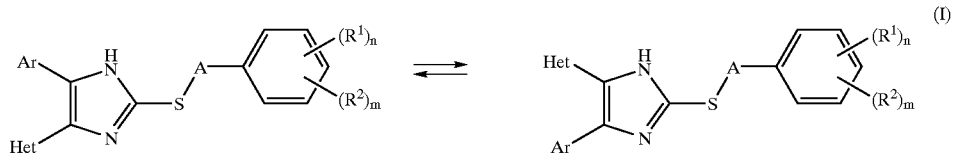

(I)

Even if only the 5-aryl-4-heteroarylimidazole derivatives of the general formula I are described in the description and in the claims for easier understanding, the present invention therefore also comprises the 4-aryl-5-heteroarylimidazole derivatives.

The present invention also relates to a process for the preparation of a compound of the general formula I, in which an imidazole-2-thione of the general formula II

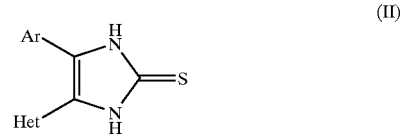

(II)

in which Ar and Het are as defined above, is reacted with a compound of the general formula III

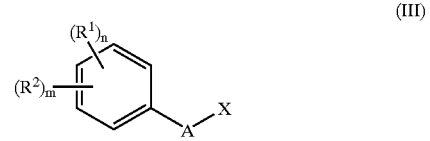

(III)

in which A, $R^1$, $R^2$, n and m are as defined above and X is a leaving group, to give a compound of the general formula I or a pharmaceutically tolerable salt thereof.

In this process, the compound according to the invention is prepared in a nucleophilic substitution reaction from corresponding aralkyl, aralkenyl or aralkynyl precursors of the formula II and the 5-aryl-4-heteroarylimidazole-2-thiones of the formula II in the presence or absence of various bases, such as sodium hydride, alkali metal hydroxide, carbonate or acetate.

The precursors of the formula III include a leaving group X, which can be, for example, chlorides, bromides, iodides, acetates or the methanesulfonic acid, toluenesulfonic acid and trifluoromethanesulfonic acid esters of the corresponding alcohols, or further leaving groups known as suitable to the person skilled in the art.

Solvents used are either dipolar aprotic solvents, in particular DMF, or protic solvents, such as alcohols, in particular ethanol but also as mixtures with ethers, such as THF.

A particularly preferred embodiment of the process is the reaction of the aralkyl, aralkenyl or arylkynyl precursors with 5-(4-fluorophenyl)-4-(4-pyridyl)-imidazolethione (CAS Reg. No. 72882-75-8) in ethanol/THF in the presence of sodium carbonate or sodium acetate at a temperature of 20–80° C.

For example, 5-(4-fluorophenyl)-2-[2-(methylsulfinyl)-benzylthio]-4-(4-pyridinyl)-1H-imidazole and 5-(4-fluorophenyl)-2-[4-(methylsulfinyl)benzylthio]-4-(4-pyridinyl)-1H-imidazoles are obtained by base-catalyzed substitution of the positionally isomeric (methylsulfinyl) benzyl chlorides with 5-(4-fluorophenyl)-4-(4-pyridyl)-1H-imidazole-2-thione.

Under the same conditions, 3-(methylsulfinyl)benzyl chloride forms no 5-(4-fluorophenyl)-2-[3-(methylsulfinyl) benzylthio]-4-(4-pyridinyl)-1H-imidazole. It is prepared by selective oxidation with $H_2O_2$ in glacial acetic acid of 5-(4-fluorophenyl)-2-[3-(methylthio-benzylthio]-4-(4-pyridinyl)-1H-imidazole, which can be prepared by substitution of 3-(methylthio)benzyl chloride by 5-(4-fluorophenyl)-4-(4-pyridinyl)-1H-imidazole-2-thione.

Differences also exist in the synthesis route for the various precursors in the case of the methylthio and methylsulfinyl compounds. Thus p-methylsulfinylbenzyl chloride is obtained from p-methylthiobenzyl alcohol by chlorination and S-oxidation. The o-methylsulfinylbenzyl chloride is accessible via the S-methyl ether of thiosalicylic acid, which is reduced to the benzyl alcohol by $LiAlH_4$, chlorinated with thionyl chloride and oxidized on the S atom using $H_2O_2$ in glacial acetic acid. m-Methylthiobenzyl chloride can likewise be prepared by chlorosulfonation, S-reduction, S-methylation, C-reduction and chlorination starting from benzoic acid. The preparation of the other intermediates of the formula III is carried out by conventional methods known to the person skilled in the art.

As a special case, 2-hydroxybenzylthio-5-(4-fluorophenyl)-4-(4-pyridinyl)-1H-imidazoles of the general formula I ($R^2$=OH) can also be prepared from suitable hydroxymethylphenols and 5-(4-fluorophenyl)-4-(4-pyridinyl)-1H-imidazole-2-thione by acid-catalyzed substitution. Corresponding alkylthiohydroxymethylphenols of the formula III are obtained from phenolcarboxylic acid esters by chlorosulfonation, S-reduction, S-alkylation and final C-reduction. The (alkylthio)benzylthioimidazoles prepared in this way can be oxidized selectively to the (alkylsulfinyl)benzylthioimidazoles using $H_2O_2$/glacial acetic acid.

The imidazole-2-thione of the general formula II also employed as a starting material in the process of the present invention can be prepared by conventional methods known to the person skilled in the art.

For example, the preparation can be carried out according to the route described by I. Lantos et al. (J. Med. Chem. 1984, 27, 72–75). According to this method, cyanohydrin benzoates, which can only be obtained in very small yields from aromatic aldehydes, are condensed with a second, aromatic aldehyde to give unsymmetrical benzoins, and these are finally ring-closed with thiourea to give the imidazole-2-thiones.

According to another method described by Bender et al. in EP 0 231 622 A2, the ring closure is carried out using azirenes which add in situ with hydrogen thiocyanate to give the desired imidazo-2-thiones.

The last-mentioned method is presently illustrated in greater detail in example 1.I.

The compounds of the formula I according to the invention show an antiinflammatory activity in vivo, and in vitro show an inhibition of the release of various cytokines, and they are suitable as inhibitors of the arachidonic acid cascade. They are thus suitable for the treatment of diseases in which increased release rates of cytokines or of the eicosanoid mediators are responsible for the origin or the progressive course of these diseases.

The present invention thus also comprises medicaments which contain a compound of the general formula I or a pharmaceutically tolerable salt thereof and, if appropriate, customary vehicles and excipients.

Furthermore, the compounds of the general formula I according to the invention are in particular also suitable for the production of medicaments for the treatment of diseases in which the increased release rate of cytokines,, such as IL-1b and TNF-α, or of the eicosanoid mediators, such as hydroperoxyeicosatetraenoic acids (HPETEs) and hydroxyeicosatetraenoic acids (HETEs), leukotrienes as products of the 5-lipoxygenase metabolic pathway and prostaglandins as products of the cyclooxygenase (1/2) metabolic pathway are responsible for the origin or the progressive course of the diseases. In particular, the compounds of the general formula I according to the invention are suitable for the production of medicaments having antiinflammatory action.

Preferably, the compounds of the general formula I according to the invention are used for the production of medicaments for the treatment of the following diseases:

rheumatoid arthritis, rheumatoid spondylitis, osteoarthritis, gout, multiple sclerosis, toxic shock syndrome, sepsis, adult respiratory distress syndrome (ARDS), inflammatory bowel disease (IBD), cachexia, AIDS-related complex (ARC), ulcerative colitis, Crohn's disease, inflammatory skin diseases and psoriatic arthritis.

The following examples are intended to illustrate the present invention in greater detail.

EXAMPLE 1

I) Intermediate Compound 5-(4-Fluorophenyl)-4-(4-pyridyl)imidazole-2-thione a) 2-Cyano-2-(4-fluorophenyl)-1-(4-pyridyl)ethen-1-ol hydrochloride 17.3 g (0.75 mol) of metallic sodium were treated dropwise with 250 ml of absolute ethanol. 75.8 g (0.5 mol) of ethyl isonicotinate and 67.6 g (0.5 mol) of 4-fluorophenylacetonitrile were added to the ethoxide. The reaction mixture was stirred at 100° C. for 15 min. The mixture was then cooled in an ice bath and treated with 600 ml of dist. water. On acidifying to pH 1 using 90 ml of conc.

HCl, the title compound deposited as a yellow precipitate. The precipitate was filtered off, washed with dist. water and dried over $P_2O_5$ in vacuo. Yield: 85.0 g (62%).

$^1$H NMR ([$D_6$]DMSO/CDCl$_3$) δ(ppm): 8.8 (AA', 2H, 4-pyridyl), 7.8 (m, 2H, 4-F-phenyl), 7.7 (BB', 2H, 4-pyridyl), 7.1 (m, 2H, 4-F-phenyl), enol signal not visible.

b) 2-(4-Fluorophenyl)-1-(4-pyridyl)ethanone 40.6 g (0.15 mol) of 2-cyano-2-(4-fluorophenyl)-1-(4-pyridyl)ethen-1-ol hydrochloride were refluxed with vigorous stirring for 19 h in 130 ml of 48% strength hydrobromic acid. The reaction mixture was cooled in an ice bath, and the precipitate deposited (4-fluorophenylacetic acid) was filtered off and washed with dist. water. On neutralizing the filtrate with 80 ml of ammonia water, the title compound deposited as a dark-green precipitate. The precipitate was filtered off, washed with dist. water and dried over $P_2O_5$ in vacuo: pale gray-beige powder. Yield: 14.2 g (45%).

$^1$H NMR (CDCl$_3$) δ (ppm): 8.8 (AA', 2H, 4-pyridyl), 7.8 (BB', 2H, 4-pyridyl), 7.2 (m, 2H, 4-F-phenyl), 7.0 (m, 2H, 4-F-phenyl), 4.3 (s, 1H, —CH$_2$—).

c) 2-(4-Fluorophenyl)-1-(4-pyridyl)ethanone oxime 21.5 g (0.1 mol) of 2-(4-fluorophenyl)-1-(4-pyridyl)-ethanone was suspended in 330 ml of 50% aqueous methanol. After addition of 36.1 g (0.44 mol) of sodium acetate and 22.0 g (0.32 mol) of hydroxylamine hydrochloride, the reaction mixture was refluxed for 1 h with stirring. On cooling in an ice bath, the title compound deposited as a beige-colored precipitate. The precipitate was filtered off, washed with dist. water and dried over $P_2O_5$ in vacuo. Yield: 14.3 g (62%).

$^1$H NMR (CDCl$_3$) δ(ppm): 11.7 (s, 1H, oxime OH) , 8.6 (AA', 2H, 4-pyridyl), 7.5 (BB', 2H, 4-pyridyl), 7.2 (m, 2H, 4-F-phenyl), 6.9 (m, 2H, 4-F-phenyl), 4.1 (s, 2H, —CH$_2$—)

d) 2-(4-Fluorophenyl)-1-(4-pyridyl)ethanone, O-[(4-methylphenyl) sulfonyl]oxime 10.1 g (0.04 mol) of 2-(4-fluorophenyl)-1-(4-pyridyl) ethanone oxime were dissolved in 50 mol of absolute pyridine in an argon atmosphere. The solution was cooled to 6° C. and treated dropwise with 10.1 g (0.05 mol) of toluenesulfonyl chloride. After addition was complete, the reaction mixture was stirred at room temperature for 20 h. The mixture was then poured onto 500 ml of ice water. The precipitate deposited was filtered off, washed in the cold with dist. water and dried at 50° C. in a drying oven. Yield: 14.9 g (88%).

$^1$H NMR (CDCl$_3$) δ(ppm): 11.7 (s, 1H, oxime), 8.6 (d, 2H, AA', 4-pyridyl), 7.9 (AA', 2H, 4-tosyl), 7.5 (BB', 2H, 4-pyridyl), 7.4 (BB', 2H, 4-tosyl), 6.9–7.1 (m, 4H, 4-F-phenyl), 4.1 (s, 2H, —CH$_2$—), 2.5 (s, 1H, —CH$_3$).

e) 5-(4-fluorophenyl) -4-(4-pyridyl) imidazole-2-thione 10.0 g (0.03 mol) of 2-(4-fluorophenyl)-1-(4-pyridyl)-ethanone, O-[(4-methylphenyl) sulfonyl]oxime were dissolved in 56 ml of absolute ethanol in an argon atmosphere. The solution was cooled to 5° C. and treated dropwise with freshly prepared sodium ethoxide from 0.75 g (0.03 mol) of metallic sodium in 30 ml of absolute ethanol. The reaction mixture was stirred at 5° C. for 5 h. After addition of 500 ml of diethyl ether, it was stirred for a further 30 min. The precipitate deposited was filtered off and washed 4× using 50 ml of diethyl ether each time. The combined ethereal phase was extracted 3× with 90 ml of 10% strength hydrochloric acid each time. The aqueous extract was concentrated to 40 ml and treated with 5.0 g (0.05 mol) of potassium thiocyanate. The reaction mixture was refluxed for 1 h with stirring. On neutralizing with 270 ml of 5% sodium hydrogencarbonate solution the title compound deposited as a beige precipitate. The precipitate was filtered off, washed with dist. water and dried at 60° C. in a drying oven. Yield: 5.6 g (79%).

$^1$H NMR ([$D_6$]DMSO) δ(ppm): 12.76 (AA', 2H, 2NH) 8.50 (AA', 2H, 4-pyridyl), 7.50–7.42 (m, 2H, 4-F-phenyl), 7.34–7.25 (m, 4H, 4-pyridyl+4-F-phenyl).

$^{13}$C NMR ([$D_6$]DMSO) δ(ppm): 164.3 162.1 160.0 149.9 135.5 130.8 130.7 126.8 124.5 121.8 120.4 116.2 115.7.

IR (KBr) 1/λ [cm$^{-1}$]: 1602, 1518, 1228, 1161, 1005, 830, 586, 545.

II) Compound according to the invention 5-(4-Fluorophenyl)-2-[(4-methylthio)benzylthio]-4-(4-pyridyl)imidazole 5-(4-Fluorophenyl)-4-(4-pyridyl)imidazole-2-thione (343 mg, 1.3 mmol), prepared by the process described above under I), was suspended in 12 ml of a 50% strength solution of ethanol in THF and treated with 123 mg (1.5 mmol) of sodium acetate. 258 mg (1.5 mmol) of (4-methylthio)benzyl chloride were introduced into this initial mixture. The reaction mixture was refluxed for 4 h with stirring. The mixture was filtered and the filtrate was concentrated. The residue was crystallized using ethyl acetate and the crystallizate was filtered off. Yield: 0.35 g (68%).

$^1$H NMR ([$D_6$]DMSO): δ(ppm) 8.46–8.43 (AA', 2H, 4-pyridyl), 7.67–7.05 (m, 11H, 4-F-phenyl), 4-CH$_3$S-phenyl, 4-pyridyl, NH$_{Im}$), 4.33 (s, 2H, —CH$_2$—), 2.45 (s, 3H, —SCH$_3$).

IR (KBr) 1/λ=cm$^{-1}$: 3429, 1606, 1579, 1504, 1424, 1226, 832.

EXAMPLE 2

5-(4-Fluorophenyl)-2-[(4-methylsulfinyl) benzylthio]-4-(4-pyridyl)imidazole 5-(4-Fluorophenyl)-4-(4-pyridyl)imidazole-2-thione from example 1.I (546 mg, 2.0 mmol) was suspended in an ethanol/THF mixture (1:1, 20 ml) and treated with sodium acetate (195 mg, 2.4 mmol). After introduction of (4-methylsulfinyl)benzyl chloride (520 mg, 2.8 mmol), the reaction mixture was refluxed for 12 h with stirring. The mixture was filtered and the filtrate was concentrated. The residue was crystallized using ethyl acetate, the crystallizate was filtered off and purified by column chromatography (cc) (SiO$_2$/methanol). Yield: 65 mg (8%).

$^1$H NMR ([$D_4$]MeOH): δ(ppm) 8.4 (AA', 2H, 4-pyridyl), 7.6 (AA', 2H, 4-CH$_3$SO-phenyl), 7.5 (BB', 2H, 4-CH$_3$SO-phenyl), 7.4–7.3 (m, 4H, 4-pyridyl, 4-F-phenyl), 7.2 (m, 2H, 4-F-phenyl), 7.4–7.1 (m, 11H, 4-F-phenyl, 4-CH$_3$S-phenyl, 4-pyridyl, NH$_{Im}$), 4.3 (s, 2H, —CH$_2$—), 2.7 (s, 3H, —SOCH$_3$).

IR (KBr) 1/λ=cm$^{-1}$: 3426, 1602, 1506, 1226, 1157, 1039, 1007, 835, 582.

EXAMPLE 3

5-(4-Fluorophenyl)-2-[(4-methylsulfonyl) benzylthio]-4-(4-pyridyl)imidazole 5-(4-Fluorophenyl)-4-(4-pyridyl)imidazole-2-thione from example 1.I (343 mg, 1.3 mmol) was suspended in a mixture of ethanol (6 ml) and THF (6 ml) and treated with sodium acetate (123 mg, 1.5 mmol). (4-Methylsulfonyl) benzyl chloride (306 mg, 1.5 mmol) were introduced into this initial mixture. The reaction mixture was refluxed for 5 h with stirring. The mixture was filtered and the filtrate was concentrated. The residue was crystallized using ethyl acetate and the crystallizate was filtered off. Yield: 0.25 g (45%).

$^1$H NMR ([D$_6$]DMSO): δ(ppm) 8.4 (AA', 2H, 4-pyridyl), 7.9 (AA', 2H, 4-CH$_3$SO$_2$-phenyl), 7.6 (BB', 2H, 4-CH$_3$SO$_2$-phenyl), 7.4–7.3 (m, 4H, 4-pyridyl, 4-F-phenyl), 7.1 (m, 2H, 4-F-phenyl), 7.4–7.1 (m, 11H, 4-F-phenyl, 4-CH$_3$S-phenyl, 4-pyridyl, NH$_{lm}$) , 4.4 (s, 2H, —CH$_2$—) , 3.0 (s, 3H, —SCH$_3$).

IR (KBr) 1/λ=cm$^{-1}$: 3426, 1602, 1575, 1506, 1304, 1147, 833, 768, 525.

EXAMPLE 4

2-[2-(4-Aminosulfonylphenyl)ethylthio]-5-(4-fluorophenyl)-4-(4-pyridyl)imidazole 5-(4-Fluorophenyl)-4-(4-pyridyl)imidazole-2-thione from Example 1.I (343 mg, 1.26 mmol) was suspended in ethanol/THF (1:1, 12 ml) and treated with sodium acetate (123 mg, 1.5 mmol). 2-(4-Aminosulfonylphenyl)ethyl chloride (282 mg, 1.3 mmol) was introduced into this initial mixture. The reaction mixture was refluxed for 5 h with stirring. The mixture was filtered and the filtrate was concentrated. The residue was crystallized using diisopropyl ether, and the crystallizate was filtered off and recrystallized from isopropanol. Yield: 0.32 g (60%).

$^1$H NMR ([D$_6$]DMSO): δ(ppm) 8.35–8.32 (d, 2H, arom.); 7.82–7.77 (d, 2H, arom.); 7.52–7.06 (m, 6H, arom.); 7.15–7.06 (t, 2H, arom.); 3.36 (t, 2H, J=7.4 Hz, CH$_2$); 3.08 (t, 2H, CH$_2$)

IR (KBr) 1/λ=cm$^{-1}$: 3347, 3251, 1603, 1505, 1335, 1222, 1158, 831, 586, 540.

EXAMPLE 5

2-[(4-Aminosulfonylphenyl)methylthio]-5-(4-fluorophenyl)-4-(4-pyridyl)imidazole 5-(4-Fluorophenyl)-4-(4-pyridyl)imidazole-2-thione from Example 1.I (1.8 g, 7.2 mmol) and (4-aminosulfonyl)benzyl bromide (1.63 g, 6.0 mmol) were suspended in ethanol (120 ml) and treated with sodium carbonate (1.14 g, 10.8 mmol). The reaction mixture was refluxed for 4 h with stirring. The mixture was filtered cold and the filtrate was concentrated. The residue was crystallized using ethyl acetate, and the crystallizate was filtered off and recrystallized from THF. Yield: 1.1 g (35%).

$^1$H NMR ([D$_6$]DMSO): δ(ppm) 8.43–8.40 (d, 2H, arom.); 7.81–7.15 (m, arom.); 4.44 (s, 2H, CH$_2$);

IR (KBr) 1/λ=cm$^{-1}$: 3431, 3045, 2926, 1604, 1508, 1304, 1145, 835, 528.

EXAMPLE 6

2-[2-(4-Methylthiophenyl)ethylthio]-5-(4-fluorophenyl)4-(4-pyridyl)imidazole 5-(4-Fluorophenyl)-4-(4-pyridyl)imidazole-2-thione from Example 1.I (406 mg, 1.5 mmol) and (2-[(4-methylthio)phenyl]ethyl chloride (350 mg, 1.87 mmol) were suspended in ethanol (30 ml) and treated with sodium carbonate (280 g, 2.7 mmol). The reaction mixture was refluxed for 48 h with stirring. The mixture was filtered cold and the filtrate was concentrated. The residue was crystallized using ethyl acetate, and the crystallizate was filtered off. Crude yield: 0.3 g (55%). Recrystallization from isopropanol yields 0.1 g of colorless substance (18%).

$^1$H NMR ([D$_6$]DMSO): δ(ppm) 8.42–8.39 (d, 2H, arom.); 7.52–7.12 (m, 10H, arom.); 3.39–3.32 (t, 2H, CH$_2$); 3.02–2.98 (t, 2H, CH$_2$); 2.43 (s, 3H, CH$_3$)

IR (KBr) 1/λ=cm$^{-1}$: 3424, 3044, 2924, 1603, 1517, 1226, 1002, 842, 831.

EXAMPLE 7

5-(4-Fluorophenyl)-2-[2-(4-methylsulfonylphenyl)ethylthio]-4-(4-pyridyl)imidazole 5-(4-Fluorophenyl)-4-(4-pyridyl)imidazole-2-thione from Example 1.I (1.63 g, 6 mmol) and 2-[(4-methylsulfonyl)phenyl]ethyl chloride (1.6 g, 7.3 mmol) were suspended in ethanol (120 ml) and treated with sodium carbonate (1.14 g, 10.8 mmol). The reaction mixture was refluxed for 60 h with stirring. The mixture was filtered cold and the filter residue was suspended in water. The water-insoluble constituents were filtered off with suction, dried and recrystallized from MeOH: yield 0.9 g.

The ethanol filtrate of the reaction solution was concentrated. The residue of this phase was crystallized using MeOH and the crystallizate was filtered off. Yield: 0.6 g Total yield: 1.5 g (55%)

$^1$H NMR ([D$_6$]DMSO): δ(ppm) 8.42 (s, 2H, arom.); 7.88–7.83 (m, 2H, arom.); 7.56–7.41 (m, 6H, arom.); 7.21–7.17 (t, 2H, arom.); 3.44–3.41 (t, 2H, CH$_2$); 3.2–3.1 (m, 5H, CH$_2$, CH$_3$)

IR (KBr) 1/λ=cm$^{-1}$: 3435, 3044, 2934, 1605, 1509, 1411, 1302, 1232, 1144, 1087, 1007, 833.

EXAMPLE 8

5-(4-Fluorophenyl)-2-[(3-methylthiophenyl)methylthio]-4-(4-pyridyl)-1H-imidazole a) 3-Chlorosulfonylbenzoic acid Benzoic acid (30.5 g, 0.25 mol) is treated with chlorosulfonic acid (10 ml/1.05 mol). The reaction mixture is heated to 120° C. in the course of 20 min with stirring. To complete the reaction, it is stirred for 45 min at 125° C. until the absence of the evolution of gas. The reaction mixture is cooled to room temperature (RT) and added to 300 ml of ice with stirring. The cream-colored precipitate is filtered off, thoroughly washed with ice water and dried. Yield: 40.8 g (74%)

$^1$H NMR ([D$_6$]DMSO) δ(ppm): 8.49 (6 variable, s, 1H, carboxyl OH); 8.28–8.24 (m, 1H, C2-H); 7.98–7.88 (m, 2H, C4-H, C6-H); 7.58–7.51 (m, 1H, C5-H)

b) Dithio-di-m-benzoic acid 90 ml of conc. hydrochloric acid are added to a solution of 3-chlorosulfonylbenzoic acid (20 g, 0.091 mol) in 135 ml of ethanol. Zinc dust (32 g, 0.49 mol) is introduced in portions in the course of 2 h into this initial mixture with stirring and initial ice-cooling. After 30 min, the cooling is removed and the reaction mixture is stirred further at RT. After addition is complete, the reaction mixture is stirred at RT for a further 3 h. The reaction mixture is filtered and the residue is washed with a little ethanol. The combined filtrates are treated in portions with solid FeCl$_3$ with stirring until the solution assumes a permanent brown coloration. On allowing to stand at RT, the title compound deposits within a few minutes as a beige precipitate. The crude product is filtered off, washed with H$_2$O and dried. Yield: 7.5 g (54%)

$^1$H NMR ([D$_6$]DMSO): δ(ppm) 8.10–8.03 (m, 2H, C2-H+C2'-H); 7.90–7.74 (m, 4H, C4-H, C6-H, C4'-H, C6'-H); 7.60–7.50 (m, 2H, C5-H. C5'-H); carboxyl OH not visible c) 3-Methylthiobenzoic acid Na$_2$S×6–9 H$_2$O (3.1 g, 14 mmol) is introduced into a solution of dithio-di-m-benzoic acid (7.5 g, 25 mmol) in 125 ml of 1N sodium hydroxide solution. The reaction mixture is heated to reflux temperature in the course of 15 min with stirring and stirred under reflux for a further 60 min. The pale brown suspension is cooled to RT and treated in portions with dimethyl sulfate (5.4 ml/56 mmol) at 30° C. The reaction mixture is stirred at RT for 2.5 h and under reflux for a further 30 min. The reaction mixture is cooled to RT, made up with 30 ml of dist. $H_2O$ and acidified dropwise to pH=1 using conc. hydrochloric acid. The pale-brown precipitate is filtered off, washed with $H_2O$ and dried. The crude product is recrystallized from 300 ml of 50% strength aqueous methanol with addition of active carbon (0.5 g) and filtered hot: silver-white flakes, yield; 3.7 g (44%)

$^1$H NMR ([$D_6$]DMSO): δ(ppm)=7.78–7.70 (m, 2H, C2-H, C4-H); 7.54–7.41 (m, 2H, C5-H, C6-H); 2.53 (s, 3H, methyl); carboxyl OH not visible $^{13}$C NMR ([$D_6$]DMSO): δ(ppm)=166.84; 138.89; 131.43; 129.98; 129.08; 125.97; 125.58; 14.46 d) 3-Hydroxymethyl-1-methylthiobenzene 95% LiAlH$_4$ (1.6 g, 40 mmol) is introduced in 75 ml of absolute THF into a 3-necked flask which is heated and flushed with argon. A solution of 3-methylthiobenzoic acid (5.2 g, 31 mmol) in absolute THF (25 ml) is added dropwise to this initial mixture with ice-cooling in the course of 15 min such that only a moderate evolution of gas takes place. After addition is complete, the cooling is removed and the reaction mixture is stirred at RT for 30 min and 60–65° C. for a further 2 h. The reaction mixture is cooled to RT and treated cautiously with ice water with ice-cooling. The precipitate of Al(OH)$_3$ is dissolved by addition of 10% strength sulfuric acid. The organic phase is separated off and the aqueous-acidic phase is extracted 3× with diethyl ether. The combined ethereal extracts are washed 2× with saturated NaCl solution and 2× with dist. $H_2O$, dried over $Na_2SO_4$ and concentrated. The oily crude product is purified by distillation in a bulb tube ($2.5 \times 10^{-2}$ mbar, 155–175° C.): colorless oil, yield: 4.5 g (94%).

$^1$H NMR (CDCl$_3$): δ(ppm)=7.32–7.10 (m, 4H, Ph—H); 4.67 (s, 2H, methylene); 2.49 (s, 3H, methyl); 1.72 (s, 1H, exchangeable, OH)

e) 3-Chloromethyl-1-methylthiobenzene

3-Hydroxymethyl-1-methylthiobenzene (3.3 g, 21 mmol) is dissolved in absolute CH$_2$Cl$_2$ (20 ml) under an argon atmosphere. A solution of SOCl$_2$ (2.6 g, 21 mmol) in absolute CH$_2$Cl$_2$ (10 ml) is added dropwise with stirring to this initial mixture in the course of 15 min, initially under reflux, then at an internal temperature of 30° C. The reaction mixture is stirred under reflux for 2.25 h. The reaction mixture is concentrated and the oily crude product is purified by bulb tube distillation ($7.9 \times 10^{-2}$ mbar, 125–140° C.): colorless oil; yield: 3.3 g (88%)

$^1$H NMR (CDCl$_3$): δ(ppm)=7.28–7.16 (m, 4H, Ph—H); 4.55 (s, 2H, methylene); 2.49 (s, 3H, methyl)

f) 5-(4-Fluorophenyl)-2-[(3-methylthiophenyl)methylthio]-4-(4-pyridyl)-1H-imidazole 3-Chloromethyl-1-methylthiobenzene (690 mg, 4.1 mmol) is dissolved in 60 ml of absolute ethanol in an argon atmosphere. 5-(4-Fluorophenyl)-4-(4-pyridyl)imidazole-2-thione (1.1 g, 4.1 mmol) is introduced into this initial mixture. The reaction mixture is stirred under reflux for 11 h. The heating is removed and the orange-colored solution is subsequently stirred at RT for 61 h. The yellow precipitate is filtered off and dried. Yield: 1.21 g (73%)

$^1$H NMR ([$D_6$]DMSO): δ(ppm)=8.67 (m, 2H, AA' 4-Pyr); 7.91 (m, 2H, BB'4-Pyr); 7.63–7.56 (m, 2H, 4-F—Ph); 7.43–7.16 (m, 6H, 4-F—Ph+3-H$_3$CS—Ph); 4.46 (s, 2H, methylene); 2.40 (s, 3H, methyl); NH not visible $^{13}$C NMR ([$D_6$]DMSO): δ(ppm)=165.05; 160.14; 148.91; 143.33; 141.29; 138.69; 138.15; 136.88; 131.30; 131.13; 130.58; 128.96; 126.21; 125.42; 124.71; 121.44; 116.46; 116.03; 35.95; 14.52

EXAMPLE 9

5-(4-Fluorophenyl)-2-[(3-methylsulfinylphenyl) methylthio]-4-(4-pyridyl)-1H-imidazole 5-(4-Fluorophenyl)-2-[(3'-methylthiophenyl)methylthio]-4-(4-pyridyl)-1H-imidazole (example 8, 500 mg, 1.2 mmol) is suspended in 7 ml of glacial acetic acid. 35% strength $H_2O_2$ solution (0.13 ml/1.3 mmol) is added dropwise to the initial mixture. The reaction mixture is stirred at RT for 20.5 h. The reaction mixture is diluted with 5 ml of $H_2O$ and adjusted dropwise to pH=9 using conc. ammonia water with ice-cooling. The aqueous supernatant is decanted off and extracted 3× with ethyl acetate. The oily residue is taken up in ethyl acetate. The organic solutions are combined, washed 3× with saturated NaCl solution, dried over $Na_2SO_4$ and concentrated. The oily crude product is purified (RP-18/MeOH) by cc: pale yellow powder, yield: 156 mg (31%).

IR (KBr): $1/\lambda [cm^{-}]$=3099, 3057, 2937, 1601, 1500, 1418, 1228, 1019, 837, 829, 694;

$^1$H NMR ([$D_3$]MeOD): δ(ppm)=8.41 (dd, 2H, J=5.0 Hz, J=1.4 Hz, AA'4-Pyr); 7.58–7.37 (m, 8H, BB'4-Pyr, 4-F—Ph, 3-H$_3$CSO—Ph); 7.21–7.13 (m, 2H, 4-F—Ph); 4.37 (s, 2H, methylene); 2.67 (s, 3H, methyl);

$^{13}$C NMR ([$D_3$]MeOD): δ(ppm)=167.0; 162.0; 150.2; 149.8; 146.6; 141.4; 133.2; 132.0; 131.9; 130.9; 125.1; 123.9; 123.0; 117.3; 116.9; 43.7; 39.6.

EXAMPLE 10

5-(4-Fluorophenyl)-2-[(2-methylsulfinylphenyl) methylthio]-4-(4-pyridyl)-1H-imidazole a) 2-Methylthiobenzoic acid Thiosalicylic acid (0.5 g, 3.2 mmol) is dissolved in 3.2 ml of 10% strength sodium hydroxide solution under an argon atmosphere. Dimethyl sulfate (0.31 ml/3.2 mmol) is added dropwise with stirring to this initial mixture at RT. The reaction mixture is stirred at RT for 15 min and under reflux for a further 60 min. The reaction mixture is cooled to RT and acidified to pH=1 using 10% strength hydrochloric acid with water-cooling. The white precipitate is filtered off, washed with $H_2O$ and dried. Yield: 520 mg (96%).

$^1$H NMR ([$D_6$]DMSO): δ(ppm)=7.91 (dd, 1H, J=7.8 Hz, J=1.3 Hz, C3-H); 7.56 (ddd, 1H, J=7.7 Hz, J=7.6 Hz, J=1.5 Hz; C5-H); 7.38–1.34 (m, 1H, C6-H); 7.22 (m, 1H, C4-H); 2.40 (s, 3H, methyl); carboxyl-OH not visible b) 2-Hydroxymethyl-1-methylthiobenzene 95% LiAlH$_4$ (1.6 g, 40 mmol) is introduced in 75 ml of absolute THF into a 3-necked flask which is heated and flushed with argon. A solution of 2-methylthiobenzoic acid (5.2 g, 31 mmol) in 25 ml of absolute THF is added dropwise with ice-cooling to this initial mixture in the course of 15 min such that only moderate evolution of gas takes place. After addition is complete, the cooling is removed and the reaction mixture is stirred at RT for 30 min and at 60–65° C. for a further 2 h. The reaction mixture is cooled to RT and treated carefully with ice-water. The precipitate of Al(OH)$_3$ is dissolved by addition of 10% strength sulfuric acid. The organic phase is separated off and the aqueous-acidic phase is extracted 3× with diethyl ether. The combined ethereal extracts are washed 2× with saturated NaCl solution and 2× with dist. $H_2O$, dried over $Na_2SO_4$ and concentrated. The oily crude product is purified by distillation in a bulb tube ($2.5 \times 10^{-2}$ mbar, 155–175° C.): colorless oil, yield: 4.5 g (94%).

¹H NMR (CDCl₃): δ(ppm)=7.39–7.36 (m, 1H, C6-H); 7.31–7.14 (m, 3H, C3-H, C4-H, C5-H); 4.76 (s, 2H, methylene); 2.49 (s, 3H, methyl); 2.03 (s, 1H, OH)

c) 2-Chloromethyl-1-methylthiobenzene

2-Hydroxymethyl-1-methylthiobenzene (3.3 g, 21 mmol) is dissolved in 20 ml of absolute CH₂Cl₂ under an argon atmosphere. A solution of SOCl₂ (2.6 g, 21 mmol) in 10 ml of absolute CH₂Cl₂ is added dropwise with stirring to this initial mixture in the course of 15 min, first under reflux, then at an internal temperature of 30° C. The reaction mixture is stirred under reflux for 2.25 h. The reaction mixture is concentrated and the oily crude product is purified by bulb tube distillation (7.9×10⁻² mbar, 125–140° C.): colorless oil; yield: 3.3 g (88%).

¹H NMR (CDCl₃): δ(ppm)=7.40–7.13 (m, 4H, Ph-H); 4.74 (s, 2H, methylene); 2.51 (s, 3H, methyl)

d) 2-Chloromethyl-1-methylsulfinylbenzene

2-Chloromethyl-1-methylthiobenzene (3.0 g, 17.4 mmol) is dissolved in 35 ml of glacial acetic acid. A solution of 35% strength H₂O₂ solution (2.15 g, 22 mmol) in 10 ml of glacial acetic acid is added dropwise in the course of 5 min to this initial mixture with ice-cooling to 3–8° C. The cooling is removed and the reaction mixture is stirred at RT for 8 h, further 35% strength H₂O₂ solution (0.15 g, 1.5 mmol or 0.1 g, 1.0 mmol) being added after 6 h and 7 h respectively. The reaction mixture is treated with ice and adjusted to pH=4 using conc. ammonia water. The white precipitate is filtered off, washed with H₂O and dried. The aqueous-acidic solution is adjusted to pH=7 using conc. ammonia water. The precipitate is filtered off, washed with H₂O and dried. The aqueous-acidic solution is extracted with ethyl acetate. The organic extract is washed 2× with 8% strength NaHCO₃ solution and 2× with saturated NaCl solution, dried over Na₂SO₄ and concentrated: yellow oil which slowly crystallizes at RT. Total yield: 3.12 g (95%).

¹H NMR (CDCl₃): δ(ppm)=8.07 (dd, 1H, J=7.8 Hz, 1.4 Hz, C6-H); 7.62 (ddd, 1H, J=7.4 Hz, J=7.2 Hz, J=1.6 Hz, C4-H); 7.52 (ddd, 1H, J=7.5 Hz, J=7.3 Hz. J=1.6 Hz, C5-H); 7.43 (dd, 1H, J=7.5 Hz, J=1.6 Hz, C3-H); 4.83 (d, 1H, J=11.7 Hz, methylene); 4.65 (d, 1H, J=11.7 Hz, methylene); 2.85 (s, 3H, methyl);

¹³C NMR (CDCl₃): δ(ppm)=145.33; 134.34; 131.56; 130.61; 130.52; 124.25; 44.06; 41.64 f) 5-(4-Fluorophenyl)-2-[(2-methylsulfinylphenyl)-methylthio]-4-(4-pyridyl)-1H-imidazole 5-(4-Fluorophenyl)-4-(4-pyridyl)-1H-imidazole-2-thione (0.28 g, 1.03 mmol) and 2-chloromethyl-1-methylsulfinylbenzene (0.18 g, 0.95 mmol) are suspended in EtOH (15 ml) under protective gas (argon) and the mixture is heated under reflux (internal temperature (IT) 77° C.) for 4 h. The mixture turns deep orange-red and clears. The mixture is then concentrated and the orange-red-colored residue is dried (0.48 g). The product is dissolved in a little warm MeOH and treated dropwise with ethyl acetate until deposition begins. Crystallization takes place slowly in the cold. Yield: 230 mg (54%).

IR (KBr): 1/λ[cm⁻¹]=3057, 2979, 2919, 2901, 2625, 1634, 1606, 1556, 1522, 1490, 1470, 1350, 1223, 1213, 1155, 1062, 1033, 969, 843, 812, 740

¹H NMR ([D₃]MeOD); δ(ppm)=8.57 (m, 2H, AA'. 4-Pyr); 8.01 (m, 2H, BB' 4-Pyr); 7.95 (d, 1H, J=7.2 Hz, C3'-H); 7.62–7.47 (m, 5H, 4-F—Ph, C4'-H, C5'-H, C6'-H); 7.33–7.24 (m, 2H, 4-F—Ph); 4.62 (d, 1H, 2J=13.6 Hz, methylene); 4.50 (d, 1H, 2J=13.6 Hz, methylene); 2.87 (s, 3H, methyl)

¹³C NMR ([D₃]MeOD): δ(ppm)=167.6; 162.7; 152.3; 145.3; 143.8; 142.3; 138.9; 136.7; 133.4; 132.8; 132.5; 132.4; 132.0; 130.7; 126.9; 125.0; 123.5; 117.9; 117.5; 43.5; 35.1

EXAMPLE 11

5-(4-Fluorophenyl)-2-[(4-hydroxy-3-methylthiophenyl)-methylthio]-4-(4-pyridyl)-1H-imidazole a) Ethyl 4-methoxybenzoate Ethyl 4-hydroxybenzoate (15.0 g, 0.09 mol) is stirred into an initial mixture of KOH (6.3 g, 0.11 mol) in dist. water (60 ml) under protective gas. Dimethyl sulfate (8.8 ml, 0.09 mol) is added dropwise to the clear solution with stirring and ice-cooling such that the temperature does not exceed 15° C. After addition is complete, the cooling is removed, and to complete the reaction the reaction mixture is stirred at RT for 45 min and under reflux for 2 h, then cooled to RT. The deposited oil is taken up in diethyl ether (50 ml). The aqueous phase separated off is extracted with diethyl ether (150 ml), and the ethereal extracts obtained are combined, washed with sodium hydroxide solution (10% strength, 50 ml) and with saturated NaCl solution, dried over Na₂SO₄ sicc. and concentrated in vacuo: colorless oil, yield: 15.7 g (97%).

¹H NMR ([D₆]DMSO): δ(ppm): 8.00 (2H, J=6.9 Hz, J=2.2 Hz, AA' 4-methyl-O—Ph); 6.92 (dd, 2H, J=6.9 Hz, J=1.8 Hz, BB' 4-H₃C—O—Ph); 4.35 (q, 2H, J=7.1 Hz, methylene); 3.86 (s, 3H, O-methyl); 1.38 (t, 3H, J=7.1 Hz, methyl).

b) Ethyl 3-chlorosulfonyl-4-methoxybenzoate

A solution of ethyl 4-methoxybenzoate (10.25 g, 57 mmol) in CCl₄ (40 ml) is cooled to −15° C. and treated dropwise with chlorosulfonic acid (10.4 ml, 156 mmol) in the course of 15 min, the temperature rising to −10° C. After addition is complete, the reaction mixture is warmed to RT with stirring in the course of 30 min and then stirred at 40–50° C. for 1.5 h. The heating is removed and the reaction mixture is stirred at RT in a gentle stream of argon for 64 h to complete the chlorination. The reaction mixture is added to a suspension of ice (25 g) in CCl₄ (50 ml) with ice-cooling and vigorous stirring. It is stirred vigorously for 3 min. The organic phase is separated off and the aqueous phase is extracted 3 times with further CH₂Cl₂ (150 ml). The combined organic extracts are washed with saturated NaCl solution, dried over Na₂SO₄ sicc. and concentrated: a crystalline, white residue of a mixture of ester and free acid in the ratio 1:1 remains, which is dried on an oil pump, yield 6.7 g (42%)

¹H NMR ([D₆]DMSO); δ(ppm): 8.63 (d, 1H, J=2.1 Hz, C2-H); 8.37 (dd, 1H, J=8.8 Hz, J=2.1 Hz, C6-H); 7.19 (d, 1H, J=8.8 Hz, C5-H); 4.41 (q, 2H, J=7.1 Hz, methylene); 4.14 (s, 3H, O-methyl); 1.41 (t, 3H, J=7.2 Hz, methyl).

c) 4-Methoxy-3-methylthiobenzoic acid

In the course of 10 min, Ph₃P (20.5 g, 78 mmol) in a suspension of the mixture of 3-chlorosulfonyl-4-methoxybenzoic acid and ethyl 3-chlorosulfonyl-4-methoxybenzoate (5.1 g, 19.3 mmol, based on the mass average of ester and acid), obtained under b) is introduced in portions into 50 ml of toluene. After addition is complete, the reaction mixture is stirred at RT for 4.5 h. The fine-crystalline precipitate (Ph₃P oxide) is filtered off and washed with toluene. The combined filtrates are extracted 4 times with 30 ml of 10% strength sodium hydroxide solution (120 ml) each time. The aqueous-alkaline extracts are combined, treated with dimethyl sulfate (2 ml/21 mmol), stirred at RT for 2 h and finally heated to boiling temperature. The reaction mixture is cooled to RT and acidified to pH 1 using 20% strength hydrochloric acid with ice-cooling. The white precipitate is filtered off, washed with dist. water and dried. Yield 2.8 g (74%)

¹H NMR ([D₃]MeOD): δ(ppm)=7.86–7.79 (m, 2H, C2-H+C6-H); 6.98 (d, 1H, J=8.4 Hz, C5-H); 3.93 (s, 3H, O-methyl); 2.43 (s, 3H, S-methyl)

d) 4-Hydroxy-3-methylthiobenzoic acid

4-Methoxy-3-methylthiobenzoic acid (0.5 g, 2.5 mmol) is suspended in 7 ml of a mixture of glacial acetic acid and 48% strength HBr (1+1). The reaction mixture is stirred under reflux for 6 h. The reaction mixture is cooled to RT and added to 20 ml of $H_2O$. The aqueous solution is adjusted to pH=2 using 10% strength $Na_2CO_3$ solution and extracted 4× using 20 ml of diethyl ether each time. The organic extracts are combined, washed 2× with saturated NaCl solution, dried over $Na_2SO_4$ and concentrated: dirty-brown oil, which crystallizes on allowing to stand at RT. The crystallizate is dried, washed with $H_2O$ with stirring, filtered off and dried. Yield: 240 mg (52%).

$^1$H NMR (CDCl$_3$): δ(ppm)=8.29 (d, 1H, J=2.2 Hz, C2-H); 8.02 (dd, 1H, J=8.5 Hz, J=2.2 Hz. C6-H); 7.05 (d, 1H, J=8.5 Hz, C5-H); 2.38 (s, 3H, methyl); carboxyl OH and phenol OH not visible $^{13}$C NMR ([D$_6$]DMSO): δ(ppm)=167.28; 158.10; 128.01; 127.03; 125.47; 122.37; 114.00 e) 4-Hydroxymethyl-2-methylthiophenol

95% LiAlH$_4$ (0.55 g, 14 mmol) is introduced in absolute THF (10 ml) into a three-necked flask which is heated and flushed with argon. A solution of 4-hydroxy-3-methylthiobenzoic acid (1.37 g; 7.4 mmol) in absolute THF (15 ml) is added dropwise to this initial mixture with ice-cooling in the course of 5 min such that only moderate evolution of gas takes place. After addition is complete, the cooling is removed and the reaction mixture is stirred at RT for 30 min and at 55–65° C. for a further 21 h. After the reaction mixture has cooled to RT, it is treated carefully with ice water with ice-cooling. The basic Al(OH)$_3$ precipitate is dissolved by addition of 10% strength sulfuric acid and the aqueous, acidic solution (pH=1) is extracted with diethyl ether (150 ml). The phenolic product is extracted from the combined ethereal extract using 2 portions of sodium hydroxide solution (10%, 50 ml). The alkaline sodium hydroxide extract is adjusted to pH=7 using hydrochloric acid (20% strength), the precipitate is taken up using diethyl ether (50 ml), and the neutral aqueous solution is extracted with diethyl ether (100 ml). The combined, ethereal extract is washed with saturated NaCl solution, dried over $Na_2SO_4$ and concentrated: a crystalline, white residue remains.

Yield: 670 mg (57%).

$^1$H NMR (CDCl$_3$): δ ppm=7.50 (d, 1H, J=2.0 Hz, C3-H); 7.24 (dd, 1H, J=8.4 Hz, J=2.0 Hz, C5-H); 6.97 (d, 1H, J=8.3 Hz, C6-H); 4.60 (s, 2H, methylene); 2.34 (s, 3H, methyl); hydroxyl OH and phenol OH not visible f) 5-(4-Fluorophenyl)-2-[(4'-hydroxy-3'-methylthiophenyl)methylthio]-4-(4-pyridyl)-1H-imidazole 5-(4-Fluorophenyl)-4-(4-pyridyl)-1H-imidazol-2-thione (200 mg, 0.7 mmol) is suspended in glacial acetic acid (5 ml) and dissolved by addition of conc. hydrochloric acid (10 drops). 4-Hydroxymethyl-2-methylthiophenol (140 mg, 0.8 mmol) is introduced into the deep orange-colored solution. The reaction mixture is stirred at RT for 2 h. The reaction mixture is diluted with dist. $H_2O$ (5 ml) and the aqueous solution is adjusted dropwise to pH=8 using conc. ammonia water. The orange-colored precipitate is washed by stirring in situ at RT for 45 min, filtered off, thoroughly washed with $H_2O$ and dried, then digested with a little methanol. The methanolic supernatant is filtered off, and the residue is again washed with methanol and dried: slightly yellowish powder, yield 140 mg (47%)

IR (KBr): $1/\lambda$[cm$^{-1}$]=3423, 3099, 3057, 1600, 1500, 1417, 1227, 1159, 1019, 837, 829, 817, 799, 694, 577;

$^1$H NMR ([D$_3$]MeOD): δ(ppm)=8.41 (2H, J=4.8 Hz, J=1.4 Hz, AA' 4-Pyr); 7.5–7.3 (m, 4H, BB' 4-Pyr+4-F—Ph); 7.21–7.12 (m, 2H, 4-F—Ph); 7.0–6.9 (m, 2H, C2'-H+C6'-H in 4'-OH—Ph); 6.69 (d, 1H, J=8.0 Hz, C5'-H in 4'-OH—Ph); 4.17 (s, 2H, methylene); 2.21 (s, 3H, methyl)

EXAMPLE 12

5-(4-Fluorophenyl)-2-[(4-hydroxy-3-methylsulfinylphenyl)methylthio]-4-(4-pyridyl)-1H-imidazole 5-(4-Fluorophenyl)-4-(4-pyridyl)-1H-imidazole-2-thione (200 mg, 0.7 mmol) is suspended in 5 ml of glacial acetic acid and dissolved by addition of 15 drops of conc. hydrochloric acid. 4-Hydroxymethyl-2-methylthiophenol (140 mg, 0.8 mmol) is introduced in portions into the orange-colored solution. The reaction mixture is stirred at RT for 2.5 h. 35% strength $H_2O_2$ solution (0.1 ml, 1 mmol) is added dropwise to the reaction mixture at RT. The reaction mixture is stirred at RT for a further 4 h. The reaction mixture is diluted with 5 ml of dist. $H_2O$ and the aqueous solution is adjusted dropwise to pH=8 using conc. ammonia water. The precipitate is washed by stirring in situ at RT for 15 min, filtered off, washed thoroughly with $H_2O$ and dried. The crude product is washed by stirring with acetone, filtered off and dried: pale orange powder, yield 170 mg (55%)

IR (KBr): $1/\lambda$[cm$^{-1}$]3435, 3117, 3063, 2360, 2325, 1604, 1503, 1425, 1296, 1280, 1230, 1160, 1062, 1013, 999, 833, 818

$^1$H NMR ([D$_3$]MeOD): δ(ppm)=8.40 (dd, 2H, J=4.8 Hz, J=1.5 Hz, AA' 4-Pyr); 7.46–7.39 (m, 5H, BB' 4-Pyr, 4-F—Ph, C2'-H); 7.28 (dd, 1H, J=8.3 Hz, J=2.2 Hz, C6'-H); 7.21–7.12 (m, 2H, 4-F—Ph); 6.78 (d, 1H, J=8.3 Hz. C5'-H); 4.28 (s, 2H, methylene); 2.70 (s, 3H, methyl)

EXAMPLE 13

2-[(5-Chloro-2-hydroxy-3-methylthiophenyl)methylthio]-5-(4-fluorophenyl)-4-(4-pyridyl)-1H-imidazole Analogously to example 11 from 5-chloro-2-hydroxy-3-methylthiobenzyl alcohol and 5-(4-fluorophenyl)-4-(4-pyridyl)-1H-imidazole-2-thione in glacial acetic acid/conc. hydrochloric acid:

$^1$H NMR ([D$_6$]DMSO): δ(ppm)=12.74 (bs, 1H, NH); 8.49 (m, 2H, AA' 4-Pyr); 7.51–7.23 (m, 6H, BB' 4-Pyr, 4-F—Ph); 7.17 (d, 1H, J=2.3 Hz, C4'-H); 6.97 (d, 1H, J=2.3 Hz, C2'-H); 4.38 (s, 2H, methylene); 2.34 (s, 3H, methyl); phenol OH not visible;

IR (KBr): $1/\lambda$[cm$^{-1}$]=3057, 2919, 2643, 2517, 1604, 1511, 1419, 1259, 1225, 1007, 988, 834, 589

EXAMPLE 14

2-[(2-Hydroxy-5-methylthiophenyl)methylthio]-5-(4-fluorophenyl)-4-(4-pyridyl)-1H-imidazole Analogously to example 11 from 2-hydroxy-5-methyl thiobenzyl alcohol and 5-(4-fluorophenyl)-4-(4-pyridyl)-1H-imidazole-2-thione in glacial acetic acid/conc. hydrochloric acid:

$^1$H NMR ([D$_7$]DMF): δ(ppm)=10.7–10.3 (bs, 1H, exchangeable, NH); 8.54 (m, 2H, AA' 4-Pyr); 7.65–7.58 (m, 2H, 4-F—Ph); 7.52 (m, 2H, BB' 4-Pyr); 7.35–7.27 (m, 3H, 4-F—Ph+C2'-H); 7.13 (dd, 1H, J=8.3 Hz, J=2.3 Hz, C4'-H); 6.90 (d, 1H, J=8.4 Hz, C5'-H); 4.46 (s, 2H, methylene); 2.36 (s, 3H, methyl); phenol OH not visible;

$^{13}$C NMR ([D$_7$]DMF): δ(ppm)=165.6; 162.9; 160.7; 155.0; 150.7; 143.5; 131.6; 131.4; 131.2; 129.8; 127.6; 126.5; 121.6; 120.0; 117.5; 116.6; 116.2; 32.5; 17.5;

IR (KBr): $1/\lambda$[cm$^{-1}$]=3057, 2913, 2661, 2607, 1602, 1511, 1486, 1418, 1382, 1275, 1255, 1230, 1158, 1005, 990, 838, 817, 590, 529

EXAMPLE 15

2-[(5-Chloro-2-hydroxy-3-methylsulfinylphenyl)methylthio]-5-(4-fluorophenyl)-4-(4-pyridyl)-1H-imidazole Analogously to example 12 from 5-chloro-2-hydroxy-3-methylthiobenzyl alcohol and 5-(4-fluorophenyl)-4-(4- pyridyl)-1H-imidazole-2-thione in glacial acetic acid/conc. hydrochloric acid/$H_2O_2$:

$^1$H NMR ([$D_3$]MeOD): δ(ppm)=8.45 (m, 2H, AA', 4-Pyr); 7.49–7.42 (m, 6H, BB' 4-Pyr, 4-F—Ph, C4'-H); 7.39 (d, 1H, J=2.6 Hz, C2'-H); 7.23–7.14 (m, 2H, 4-F—Ph); 4.39 (s, 2H, methylene); 2.72 (s, 3H, methyl)

IR (KBr): 1/λ[$cm^{-1}$]=3420, 3057, 2997, 2925, 2823, 2655, 2517, 2457, 2360, 1605, 1509, 1416, 1392, 1265, 1236, 1158, 1086, 1051, 1005, 832, 595, 534

EXAMPLE 16

2-[(2-Hydroxy-5-methylsulfinylphenyl)methylthio]-5-(4-fluorophenyl)-4-(4-pyridyl)-1H-imidazole Analogously to example 12 from 2-hydroxy-5-methylthiobenzyl alcohol and 5-(4-fluorophenyl)-4-(4-pyridyl)-1H-imidazole-2-thione in glacial acetic acid/conc. hydrochloric acid/$H_2O_2$:

$^1$H NMR ([$D_3$]MeOD): δ(ppm)=8.41 (m, 2H, AA', 4-Pyr); 7.47–7.41 (m, 6H, BB' 4-Pyr, 4-F—Ph, C2'-H, C4'-H); 7.21–7.11 (m, 2H, 4-F—Ph); 6.96 (d, 1H, J=8.2 Hz, C5'-H); 4.33 (s, 2H, methylene); 2.60 (s, 3H, methyl);

$^{13}$C NMR ([$D_3$]MeOD): δ(ppm)=166.87; 161.95; 160.11; 150.28; 143.07; 134.91; 132.01; 131.85; 128.58; 127.73; 127.72; 126.37; 122.99; 117.58; 117.22; 116.78; 43.45; 34.57

IR (KBr): 1/λ[$cm^{-1}$]=3410, 3129, 3069, 2991, 2913, 2360, 1603, 1571, 1500, 1422, 1280, 1232, 1157, 1078, 1031, 1003, 826, 697, 586

Activity Tests

Test System for Determining the Inhibition of 5-lipoxygenase (5-LO)

The source used for the 5-lipoxygenase is human granulocytes. By stimulation with calcium ionophore A 23187, $LTB_4$ (leukotriene $B_4$) is formed from endogenous arachidonic acid. The granulocytes are isolated and the enzyme reaction is carried out according to known processes (see Arch. Pharm. Pharm. Med. Chem. 330, 307–312 (1997)).

The blood protected from clotting by heparin is centrifuged on a discontinuous Percoll® gradient and the granulocyte layer is removed by pipette. After lysis of the erythrocytes, the granulocytes are washed a number of times and then adjusted to a specific cell count. The enzyme reaction is then started in the presence or absence of the test substance after addition of $Ca^{2+}$ using calcium ionophore A 23187. The synthesis of the leukotrienes is stopped after 1.5 minutes. The samples are centrifuged off and the supernatant is diluted. $LTB_4$ is determined quantitatively by means of ELISA.

Test System for Determining the Inhibition of Cyclooxygenase-1 (COX-1)

In this test system, the amount of prostaglandin $E_2$ formed by human platelets after addition of calcium ionophore is determined by means of ELISA. The platelets are obtained here after centrifugation on a discontinuous Percoll® gradient. The enzyme reaction and the determination of the metabolites formed are in principle carried out as in the determination of the inhibition of 5-lipoxygenase. Differences exist with respect to the incubation time. Furthermore, the addition of a thromboxane synthase inhibitor is necessary (see Arch. Pharm. Pharm. Med. Chem. 330, 307–312 (1997)).

Test System for Determining the Inhibition of Cyclooxygenase-2 (COX-2)

COX-2 (from sheep placenta) is preincubated with test substance for 10 min at 4° C., then stimulated with arachidonic acid (5 μm) at 25° C. for 10 min. The reference used is diclofenac ($IC_{50}$ (COX-2)=3.0 $10^{-6}$ M). Determination is carried out 3 dilutions ($10^{-7}$, $10^{-6}$, $10^{-5}$ molar). The $PGE_2$ concentrations are quantified by means of ELISA (see Mitchell J. A. et al. Proc. Nat. Acad. Sci 90: 11693–11697 (1993)).

Test System for Determining the Inhibition of LPS-stimulated Cytokine Secretion (TNF-α, IL-1β)

Human PBMC (peripheral blood mononuclear cells) are preincubated with test substance for 5 min at 37° C., then stimulated with LPS (1 μg/ml) for 24 h at 37° C. The cytokines TNF-α, IL-1β, IL-6 and IL-8 are Determined by means of ELISA (see Blood 75, 40–47 (1990)).

Test System for Determining the Inhibition of LPS-stimulated Cytokine Secretion (TNF-α, IL-1β) in Whole Blood Fresh, human whole blood from healthy donors is preincubated with test substance for 25 min at 37° C. The cells are stimulated with LPS (1 μg/ml) for 4 h at 37° C. In the plasma supernatant which is isolated by centrifugation, the cytokines TNF-α, IL-1β, IL-6 and IL-8 are quantified by means of ELISA (see Inflamm. Res. 44, 269–274 (1995)).

The results of the activity tests carried out using the test systems described above are summarized in tables 1 and 2. The tables show the influence of the compounds according to the invention of examples 1–7, 9, 10, 12 and 16 on the release of the inflammatory mediators COX-1, COX-2, 5-LO, TNF-α and IL-1β (table 1) in comparison with the reference substances A and B (table 2), whose structure is likewise indicated in table 2.

The reference substances A and B were synthesized according to the procedure described in WO 93/14081 (p. 35, examples 19 and 20 therein).

TABLE 1

Influence of the test compounds on the release
of inflammatory mediators ($IC_{50}$ values in μmol):

| Example | Structure | COX-1 | COX-2 | 5-LO | TNFα | IL-1β |
|---------|-----------|-------|-------|------|------|-------|

Z =

TABLE 1-continued

Influence of the test compounds on the release of inflammatory mediators (IC$_{50}$ values in μmol):

| Example | Structure | COX-1 | COX-2 | 5-LO | TNFα | IL-1β |
|---|---|---|---|---|---|---|
| 1 | Z-CH₂-C₆H₄-S-CH₃ | 3.4 | 6.1 | 0.065 | PBMC: 10.0 Whole blood method: 30 | PBMC: >100.0 Whole blood method: 30 |
| 2 | Z-CH₂-C₆H₄-S(O)-CH₃ | — | 6.3 | 10 | PBMC: 6.8 Whole blood method: 16 | PBMC: 2.3 Whole blood method: 2.9 |
| 3 | Z-CH₂-C₆H₄-SO₂-CH₃ | — | — | 0.8 | PBMC: 4.0 Whole blood method: 19 | PBMC: >100 Whole blood method: 1.2 |
| 4 | Z-CH₂CH₂-C₆H₄-SO₂-NH₂ | 2.2 | 7.0 | 0.085 | PBMC: 3.3 | PBMC: 9.3 |
| 5 | Z-CH₂-C₆H₄-SO₂-NH₂ | 0.038 | 10.0 | 2.8 | PBMC: 3.1 | PBMC: 18 |
| 6 | Z-CH₂CH₂-C₆H₄-S-CH₃ | 6.5 | 3.0 | <0.01 | PBMC: 6.0 | PBMC: 58 |
| 7 | Z-CH₂CH₂-C₆H₄-SO₂-CH₃ | — | — | — | PBMC: 14 | PBMC: 21 |
| 9 | Z-CH₂-C₆H₄-S(O)-CH₃ (meta) | | | | Whole blood method: 24 | Whole blood method: 1.9 |
| 10 | Z-CH₂-C₆H₄-S(O)-CH₃ (ortho) | | | | Whole blood method: 48 | Whole blood method: 4.0 |
| 12 | Z-CH₂-C₆H₃(OH)-S(O)-CH₃ | | | | Whole blood method: 9.0 | Whole blood method: 12.1 |
| 16 | Z-CH₂-C₆H₃(OH)-S(O)-CH₃ | | | | PBMC: 4.2 Whole blood method: 76 | PBMC: 0.64 Whole blood method: 13 |

TABLE 2

Influence of the reference substances on the release of inflammatory mediators (IC$_{50}$ values in µmol)

| | | |
|---|---|---|
| Reference A<br>SB 203580 | 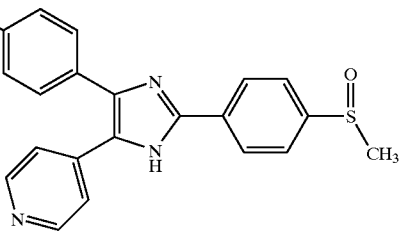 | PBMC: 1.4<br>Whole blood method: 1.8    PBMC: 0.1<br>Whole blood method: 0.3 |
| Reference B | 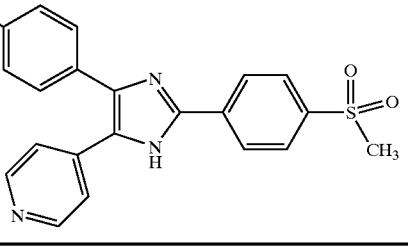 | PBMC: 7.5 |

What is claimed is:

1. A compound of formula I

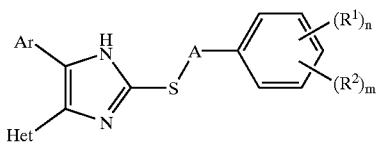

in which

Ar is a phenyl radical which can optionally be substituted by one or more substituents, selected from halogen, $C_{1-4}$-alkyl, $C_{1-4}$-alkoxy and $C_{1-4}$-alkylthio;

Het is a pyridyl which can optionally be substituted by one or more substituents selected from halogen, amino, $C_{1-4}$-alkylamino, $C_{1-4}$-alkyl, hydroxyl, $C_{1-4}$-alkoxy or $C_{1-4}$-alkylthio;

A is a straight-chain or branched, saturated or unsaturated alkylene chain having up to 6 carbon atoms;

R$^1$ is $C_{1-4}$-alkylthio, $C_{1-4}$-alkylsulfinyl, $C_{1-4}$-alkylsulfonyl, or sulfonamido;

R$^2$ is halogen, $C_{1-4}$-alkyl, hydroxyl, $C_{1-4}$-alkoxy, $C_{1-4}$-alkoxycarbonyl, sulfonamido, carboxyl, nitro or aminocarbonyl;

n is 1 or 2; and m is 0 to 2, or a pharmaceutically tolerable salt thereof.

2. A compound as claimed in claim 1, in which the heteroaromatic radical Het is a 4-pyridyl, or a 3-amino-4-pyridyl group.

3. A compound as claimed in claim 1, in which the phenyl radical Ar is substituted by one or more substituents selected from fluorine, chlorine, bromine, $C_{1-4}$-alkyl, $C_{1-4}$-alkoxy, or $C_{1-4}$-alkylthio.

4. A compound as claimed in claim 3, in which the substituent or the substituents for Ar are selected from fluorine, chlorine, methoxy and methylthio.

5. A compound as claimed in claim 4, in which the phenyl radical Ar is a 4-fluorophenyl group.

6. A compound as claimed in claim 1, in which n is 1.

7. A compound as claimed in claim 1, in which the phenyl radical Ar is a 4-fluorophenyl group, the heteroaromatic radical Het is a 4-pyridyl group, A is methylene or ethylene and n is 1.

8. A compound as claimed in claim 1, selected from the group consisting of:

5-(4-fluorophenyl)-2-[(4-methylsulfanylphenyl)methylsulfanyl]-4-pyridylimidazole;

5-(4-fluorophenyl)-2-[(4-methylsulfinylphenyl)methylsulfanyl]-4-pyridylimidazole;

5-(4-fluorophenyl)-2-[(4-methylsulfonylphenyl)methylsulfanyl]-4-pyridylimidazole;

2-[(4-aminosulfonylphenyl)methylsulfanyl]-5-(4-fluorophenyl)-4-pyridylimidazole;

2-[2-(4-aminosulfonylphenyl)ethylsulfanyl]-5-(4-fluorophenyl)-4-pyridylimidazole;

5-(4-fluorophenyl)-2-[2-(4-methylsulfanylphenyl)ethylsulfanyl]-4-pyridylimidazole;

5-(4-fluorophenyl)-2-[2-(4-methylsulfonylphenyl)ethylsulfanyl]-4-pyridylimidazole;

5-(4-fluorophenyl)-2-[(3-methylsulfanylphenyl)methylsulfanyl]-4-pyridylimidazole;

5-(4-fluorophenyl)-2-[(2-methylsulfanylphenyl)methylsulfanyl]-4-pyridylimidazole;

5-(4-fluorophenyl)-2-[(3-methylsulfinylphenyl)methylsulfanyl]-4-pyridylimidazole;

5-(4-fluorophenyl)-2-[(2-methylsulfinylphenyl)methylsulfanyl]-4-pyridylimidazole;

5-(4-fluorophenyl)-2-[(4-hydroxy-3-methylsulfanylphenyl)methylsulfanyl]-4-pyridylimidazole;

5-(4-fluorophenyl)-2-[(4-hydroxy-3-methylsulfanylphenyl)methylsulfanyl]-4-pyridylimidazole;

2-[(5-chloro-2-hydroxy-3-methylsulfanylphenyl)methylsulfanyl]-5-(4-fluorophenyl)-4-pyridylimidazole; and 2-[(5-chloro-2-hydroxy-3-methylsulfinylphenyl)methylsulfanyl]-5-(4-fluorophenyl)-4-pyridylimidazole.

9. A process for the preparation of a compound of formula I as claimed in claim 1, in which an imidazole-2-thione of formula II

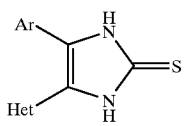
(II)

in which Ar and Het are as defined in claim 1, is reacted with a compound of formula III

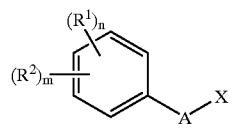
(III)

in which A, $R^1$, $R^2$, n and m are as in claim 1 and X is a leaving group, to give a compound of formula I or a pharmaceutically tolerable salt thereof.

10. A pharmaceutical composition comprising a pharmaceutically effective amount of a compound of formula I as claimed in claim 1 or a pharmaceutically tolerable salt thereof and a pharmaceutically acceptable carrier.

11. A method for treating inflamation comprising administering to a subject in need thereof, a pharmaceutically effective amount of a compound according to claim 1.

12. A method for inhibiting release of cytokines comprising administering to a subject in need thereof, a pharmaceutically effective amount of a compound according to claim 1.

13. A method for treating a disease selected from the group consisting of rheumatoid arthritis, rheumatoid spondylitis, osteoarthritis, gout, toxic shock syndrome, sepsis, adult respiratory distress syndrome (ARDS), inflammatory bowel disease (IBD), cachexia, ulcerative colitis, Crohn's disease, inflammatory, skin diseases and psoriatic arthritis, comprising administering to a subject in need therof suffering from said disease, a pharmaceutically effective amount of a compound according to claim 1.

14. The compound 2-[(4-aminosulfonylphenyl)-methylthio]-5-(4-fluorophenyl)-4-pyridyl)imidazole.

\* \* \* \* \*